United States Patent [19]

Ford

[11] 4,255,517

[45] Mar. 10, 1981

[54] LYSOZYME ASSAY

[76] Inventor: Larry C. Ford, 3278 Sawtelle Blvd., #3, Los Angeles, Calif. 90066

[21] Appl. No.: 9,379

[22] Filed: Feb. 2, 1979

Related U.S. Application Data

[63] Continuation-in-part of Ser. No. 943,773, Sep. 20, 1978, abandoned.

[51] Int. Cl.$^3$ .............................................. C12Q 1/34
[52] U.S. Cl. .................................. 435/18; 435/810; 435/4; 23/230 B; 424/2
[58] Field of Search .................... 435/4, 18, 810, 805; 424/2; 23/230 B

[56] References Cited

U.S. PATENT DOCUMENTS 3,834,991   9/1974   Megraw et al. ...................... 435/18

OTHER PUBLICATIONS

Prasad et al., "Measurement of the Lytic Activity of Lysozymes (Muramidases)", *Analytial Biochemistry*, vol. 6 (1963) pp. 328–334.

Davies et al., "The Dependence of Lysozyme Activity on pH and Ionic Strength", *Biophys Acta*, vol. 178 (1969) pp. 294–305.

Sapse et al., "Human Tear Lysozyme", *Am. J. Opthal*, vol. 66 (1968) pp. 76–80.

Bonauida, et al., "Human Tear Lysozyme", *Am. J. Opthal*, (1968) pp. 70–76.

Ford, et al., "Identification of a Bnetericidal Factor (B–Lysin) in Amniotic Fluid at 14 and 40 Weeks Gestation", *Am. J. of Obstet & Gynocol*, vol. 127, pp. 788–92.

Ford, et al., "Detection of Amiotic Fluid in the Vaginal Vault by Lysozyme Concentration", copy of talk presented at the ACOG Districts VI and VII meeting on Sept. 21, 1977, San Francisco, CA.

Grossowiz, et al., "Improved Lysozyme Assay in biological Fluids", *Clin. Chem.* vol. 25, No. 3 (1979) pp.484–5.

*Primary Examiner*—Thomas G. Wiseman
*Attorney, Agent, or Firm*—K. H. Boswell

[57] ABSTRACT

A new and improved assay for the determination of the enzyme lysozyme in biological samples which utilizes a plate assay based upon the bacterium *Micrococcus lysodiekticus* is described. The assay utilizes a novel composition for the assay medium which results in a reduction in assay incubation time to the point that the assay is complete after one-half hour. This reduction in time is achieved in part by the utilization of organic buffers in the assay medium and in part by the reduction of the ionic strength of the assay medium. by the use of this assay a novel technique for determining the integrity of the amniochorial membrane and maturity of fetal lungs are described.

22 Claims, No Drawings

LYSOZYME ASSAY

CROSS-REFERENCE TO RELATED APPLICATIONS

This application is a continuation-in-part of my application Ser. No. 943,773 filed Sept. 20, 1978, abandoned and entitled "LYSOZYME DETERMINATION TEST" the disclosure of which is herein incorporated by reference.

BACKGROUND OF THE INVENTION

Variations in the content of the enzyme lysozyme have been detected in various body fluids and tissues. Many of these variations have been correlated with certain body functions and/or malfunctions or diseased states. For example, it has been reported in the medical literature that elevated levels of lysozyme in serum and/or urine have been shown to be coincidental with megaloblastic anemia, monocytic and monomyelocytic leukemia, polycythemia vera, and acute myelogenous leukemia. Further, the lysozyme concentration has been shown to be elevated in the synovial fluid of patients with rheumatoid arthritis. During pregnancy because lysozyme is not indigenous to the vaginal cavity the mere presence of lysozyme in vaginal fluid is accepted as an indicator of the presence of amniotic fluid in the vagina because lysozyme is known to be a constituent of the amniotic fluid. If lysozyme is therefore found in the vaginal fluid it can be taken as an indicator that a rupture has occurred in the amniochorial membranes. From these facts it is clear that a reliable, rapid, facile and inexpensive lysozyme assay would be useful as a clinical diagnostic tool.

The research scientist has at his disposal many sophisticated machines and techniques to help him determine enzyme concentrations in various fluids. Certain of these machines or techniques have been used to assay lysozyme in biological fluids and tissues. These techniques and machines, however, are not suitable for routine clinical use for one or more of the following reasons: the technique is too slow; the technique is often cumbersome to perform; the technique requires the purchase of and maintenance of expensive equipment which also necessitates having available experienced technicians; the technique or the tool requires too large an amount of test tissue or biological fluid as well as other associated factors.

In *Identification of a Bactericidal Factor (B-Lysin) in Amniotic Fluid at 14 and 40 Weeks Gestation*, 788, No. 7, Volume 127, *Am. J. of Obstetrics and Gynocology*, 1977, I described a technique for determining the lysozyme concentration in an amniotic fluid. While this technique is useful for detecting lysozyme in amniotic fluid it is not susceptible to broad clinical use because of the equipment necessary in performance thereof.

A clinical method for determining the lysozyme content in human tears has been described by B. Bonavida and A. T. Sapse in *Human Tear Lysozyme*, 66, *Am. J. of Opthal.*, 70 (1970). The Bonavida technique utilizes the action of lysozyme on the cell walls of *Micrococcus lysodiekticus*. The M. lysodiekticus is suspended in an agrose solution made up in a sodium chloride and sodium phosphate buffer which also contains sodium azide. Detection of the lysozyme action on the cell walls of *M. lysodiekticus* using this technique requires incubation at 37° C. for 24 hours. This technique requires at least a minimum period of four hours to even observe the first sign of lysis caused by the lysozyme and the before mentioned 24-hour incubation period to assure reliable results.

In many clinical situations wherein a lysozyme assay would be useful as a diagnostic tool this 24-hour incubation period essentially negates the possibility of using this assay. For example, if rupture of the amniochorial membranes should occur infection of the fetus may result. In the present clinical management of such a rupture it is considered best to initiate either delivery of the fetus or appropriate antibiotic treatment of both the fetus and the mother at at least 12 hours and no later than 16 hours after rupture. The 24-hour incubation period of the Bonavida technique therefore renders this technique inappropriate in this clinical situation.

SUMMARY OF THE INVENTION

In view of the above it is therefore an object of this invention to describe a new and useful improvement of the previously described lysozyme assays which is useful on a small sample of either biological fluid and/or tissue, gives a rapid result and is simple enough in its construction and use to be used in a clinical situation utilizing normal clinical personnel.

In obtaining this broad object there is described in this specification a composition useful in a rapid lysozyme assay, a process of using this composition in the lysozyme assay, a method of determining the integrity of the amniochorial membrane, and a test for fetal lung maturity. In fulfilling the above objects this invention extends the usefulness of a lysozyme assay to many clinical situations in which a determination of lysozyme in the biological sample is useful but which could not previously be determined because the prior known existing lysozyme assay techniques were either too slow, required too large a sample, were too sophisticated for the clinical situation, or were too expensive.

The present invention describes a lysozyme assay procedure and a composition which is reliable, facile, inexpensive and affords an adequate lysozyme determination in about 30 minutes instead of the 24-hour determination time required by the previously discussed lysozyme assays. Further, the present invention gives the clinician a tool for determining the integrity of the amniochorial membrane and a tool for determining fetal lung maturity.

DETAILED DESCRIPTION

The lysozyme assay composition and process disclosed in this specification makes use of the selected action of lysozyme in a biological sample on the cell walls of the bacterium *Micrococcus lysodiekticus* by enzymatically hydrolyzing the mucopeptide N-acetal glucosamine $\beta$ (1-4) N-acetyl muramic acid at the $\beta$ (1-4) linkage. In the present invention the *M. lysodiekticus* is suspended in agarose; however, the suspending solution, i.e., the buffer used, is a new and novel improvement which so changes the medium such that the enzymatic action of the lysozyme on the bacteria is enhanced to the point that it affords an accurate clinically useful enzyme determination with a 30-minute period as opposed to the previous 24-hour incubation period required by the assay method which was previously utilized utilizing *M. lysodiekticus* in agarose. According to the teachings of the present invention the enzymatic action of lysozyme on *M. lysodiekticus* is accelerated by using a suspending buffer solution of lowered ionic strength coupled with using an organic or organic-inorganic buffer in place of the previous standard use of an inorganic buffer which had a high ionic strength resulting from sodium chloride being present in the suspending medium. While the exact mechanism accountable for this is not known it is believed that by using a suspended medium of lower ionic strength that the diffusion of lysozyme out of the biological sample into the bacteria suspension is facilitated and there is an increase in osmatic fragility of the *M. lysodiekticus* and as a result lysozyme action on the bacterial cell wall is enhanced to such an extent that the time required to determine the level of lysozyme in a biological sample is reduced to about 30 minutes.

The new and improved compositions for a lysozyme assay consists of from about 0.05 percent to about 5 percent agarose which is dissolved in from about 0.001 M to about 0.5 M organic or organic-inorganic buffer. Further, the buffer also contains from about 0.05 percent to about 0.1 percent bactericidal agent. The pH of the buffer is from about 6 to about 7 and the ionic strength of the buffer is from about 0.5 to about 0.1. Preferably the pH of the buffer is from about 6.3 to about 6.5 and the agarose concentration is about 0.5 percent, the *Micrococcus lysodiekticus* concentration is about 0.05 percent and the buffer is about 0.05 M and has an ionic strength of about 0.05.

Suitable for use as a buffer is a member selected from the group consisting of tris(hydroxymethyl)aminomethane maleate, citrate, and citrate-phosphate. Other buffers useful for the invention might also include imidazole-hydrochloride-sodium hydroxide and cacodylate. Preferably tris(hydroxymethyl)aminomethane maleate is used. Suitable as the bactericidal agent are sodium azide or thimerosal. However, other bactericidal agents soluble in the buffers within the pH range outlined might also be used.

The composition is prepared by dissolving the agarose in the buffer solution by heating to about 100° C. After cooling to about 60° C. the bactericidal agent is added followed by a suspension of *Micrococcus lysodiekticus* in the appropriate amounts to bring the final concentration of the agarose, bactericidal agent and the bacterium to the above outlined concentrations. The *Micrococcus lysodiekticus* is used in an attenuated or killed state inasmuch as the action of lysozyme is upon the bacterium cell wall. In place of the whole bacterium a suspension of only *M. lysodiekticus* cell walls could be substituted; however, at this time the whole cells are less expensive and therefore it is preferred to use the whole cell. After preparation of the appropriate mixture of ingredients a suitable volume is poured into a suitable container such as a Petrie dish. Typically a sample of 5 mls. is poured into a 60 by 15 mm. dish. This results in a layer of about 2 mm. thick. After cooling to room temperature the contents will solidify. The so prepared contents hereinafter called lysoplates can be pre-prepared in large quantities and stored for later use. Normal storage at 4° C. allows for the clinician to maintain a suitable supply of lysoplates to be kept on hand for routine use over a period of months.

While it is not deemed absolutely mandatory, normal use of the lysoplates will be facilitated by running a standard along with the biological sample to be tested. Said standard can be pre-prepared by taking a known concentration of standard commercially available lysozyme such as three times crystalline egg-white lysozyme or other suitable lysozyme and preparing standard solutions therefrom as is well known in the art.

The process for detecting and qualifying the content of the enzyme lysozyme in a biological sample consists of taking a standard quantity of the biological sample and placing said standard quantity on the surface of the assay medium of the lysoplate. Concurrently placed on the surface is also a measured quantity of the standard lysozyme solution. The lysoplate is then incubated. Normally the incubation will be performed at 37° C.; however, incubation within the ranges of from about 25° C. to about 40° C. could also be used. Above about 40° C. the enzyme is heat inactivated and below 25° C. the reaction time is inhibited.

The lysoplates are normally incubated for about 30 minutes time at 37° C. At 30 minutes time both a qualitative and quantitative reading of the lysoplate can be made. Longer incubation times of course could be used. However, they are not necessary for interpretation of the lysoplate. In an extreme emergency situation a qualitative impression of the amount and/or presence of lysozyme could be determined at an interval of time shorter than 30 minutes. Normally the incubation period would be for at least 20 minutes to about 60 minutes and preferably for about 30 minutes. At the conclusion of the incubation period the lysoplate is observed for the presence of a clear or light colored film of lysis surrounding and radiating as a concentric circle from the spot where the biological sample was applied on the lysoplate. Quantitative lysozyme determination is then made by comparing the zone of lysis of the test specimen to the zone of lysis of the standard lysozyme specimen. If a standard quantity such as 5 $\mu$l is consistently used such as would be used in the routine determination of one particular type of biological sample the zone of lysis of the biological sample can be established and standard zone sizes be assigned to indicate the lysozyme concentration without the necessity of comparison to a lysozyme standard. Preferably though since deviations from standard procedures will sometimes be encountered because of human error in incubation time, sample selection, etc., concurrently running a standard is preferred.

Normally the sample size of biological sample necessary will be from about 5 $\mu$l to about 10 $\mu$l. Larger sample sizes could, of course, be used and samples down to 1 $\mu$ can also be determined. When the biological sample is not of such a nature that accurate volumetric collection is possible or the conditions under which the sample must be obtained are such that volumetric selection is not possible the sample can be collected by contacting the surface to be sampled with portions of porous paper which are pre-calibrated to absorb known quantities of sample. Typically these pre-calibrated porous papers will be chosen such that they absorb 5 $\mu$l of sample.

The pre-calibrated paper is exposed to the point where the sample will be collected such as contacting the walls of the vagina near the posterior fornix with such a piece of pre-calibrated porous paper and then removing the paper and placing the paper directly on the surface of the lysoplate. Additionally if the sample is collected by pipette or capillary techniques instead of pipetting the sample directly onto the surface of the lysoplate the sample is pipetted onto the surface of a piece of porous paper which was gently placed on the surface of the lysoplate. This markedly decreases bubbling and spillage of test fluid which might cause an irregular shaped lytic zone that might be difficult to interpret.

Spontaneous rupture of the amniochorial membranes may be diagnosed by the gross pooling of amniotic fluid in the vaginal vault. If gross amounts of fluid are present of course there is no problem ascertaining which clinical regimen to follow. However, frequently there arises an occasion when the status of the fetal membrane is in question. The importance of determining this status is attested by the marked increase in both maternal and fetal morbidity related to infection. As was noted above, current thinking requires that therapy be initiated as soon as possible and preferably within 12 hours of the suspected rupture of the membrane. It has been shown that the incidence of complication increases directly with the length of the latent period between the spontaneous rupture of the membranes and the onslaught of labor and delivery of the infant. The optimal therapeutic regimen can only be instigated if the integrity of the amniochorial membranes is established with certainty.

A further embodiment of the present invention encompasses a method of determining the integrity of the amniochorial membranes which includes collecting a sample of about 5 $\mu l$ of vaginal fluid. If sufficient fluid is not present in the vaginal vault the required fluid can be collected on a pre-calibrated porous paper by exposing the paper to the surface of the vaginal vault. The paper is then placed on the surface of a lysoplate as previously described and a standard can also be placed if desired. The lysoplate is incubated at 37° C. for about 30 minutes and the lysozyme concentration determined by comparing the size of the zone of lysis of the vaginal fluid sample with the standard or with a predetermined value. Since lysozyme is not a normal constituent of the vaginal fluid the clinician can rapidly determine the integrity of the membrane by the amount of lysozyme present and detected by the method.

EXAMPLE

A comparison of 300 normal term pregnant patients divided into three groups of 100 individuals is tabulated to demonstrate the effectiveness of using the lysoplates. Group 1 consisted of patients in active labor who denied any history of gross rupture of the fetal membrane. Group 2 consisted of patients at term but not in active labor and who also denied any history of membrane rupture. Group 3 consisted of patients having a history of clinically ruptured membranes. The lysoplate method was compared with the arborization method as described in the literature and also the pH method as described in the literature. Further, artificial samples of amniotic fluid diluted with blood were prepared wherein the ratio of amniotic fluid to blood was 5:1, 10:1, 20:1, 50:1, 100:1.

The arborization method entails placing of a sample of vaginal fluid (about 0.5 ml.) on a dry microscope slide. The slide is allowed to dry at room temperature and then observed for the characteristic arborization or fern pattern which is looked for in this method. The pH method was measured by placing a sample of fluid on standard laboratory nitrazine pH papers. As is known by those skilled in the art the pH method because of its lack of reliability can only be used as a supplement to an alternate method.

In group 1 the pH test showed 13 patients having a positive indication of amniochorial membrane fracture, the lysozyme test was positive in ten of these patients, and the arborization test showed 5 positives. All patients who were arborization positive were also pH and lysozyme positive. Of the patients who were negative for arborization but positive for pH and lysozyme 4 of them had fluids that were bloodied and one was grossly infected. The three patients that were pH positive but lysozyme negative were observed throughout labor and delivery and clinically had a bulging forebag and copious amounts of amniotic fluid at the time of artificial rupture of the membrane. However, this does not rule out a high small leak in the fetal membranes.

Of the group 2 patients 7 were pH positive, 5 were lysozyme positive and 3 were arborization positive. As with the patients of group 1 all the patients who had a positive arborization test also had a positive pH and lysozyme test.

In most of the group 3 patients a copious amount o amniotic fluid was observed in the vaginal vault. Both the pH and the lysozyme tests were positive in all of these patients. However, the arborization was only positive in 91%. Of the 9 patients that were arborization negative 7 were bloody and 2 were frankly infected.

In the artificial samples prepared by mixing amniotic fluid with blood all of the samples having the dilutions of 5:1, 10:1 and 20:1 were arborization negative but lysozyme positive. It was only in the samples that were diluted 50:1 and 100:1 that showed the correct arborization positive test as well as the expected positive lysozyme test. The lysozyme test was able to discriminate even though the samples contained large amounts of blood, i.e., the 5:1 dilutions.

Still a further embodiment of the present invention encompasses a method of determining fetal lung maturity. A sample of amniotic fluid is placed on the surface of a lysoplate as previously described. The lysoplate is incubated at 37° C. for 30 minutes and the size of the zone of lysis is determined.

It has been pointed in the medical literature that one of the most clinically useful methods of determining fetal lung maturity is the ratio of the amount of lecithin to sphingomyelin. Normally at about 35 weeks gestation time this ratio increases to about 2. At this point it has been clinically determined that the fetal lung is mature and if delivery should take place at or after this time the chance of infant survival is increased. The lysoplate method herein described has been found to correlate with the lecithin-sphingomyelin ratio hereinafter called L/S ratio. Thus when the L/S ratio is less than 2 I have found that the lysozyme concentration is less than 12 $\mu g$ per $\mu l$ of amniotic fluid. If the L/S ratio is greater than 2 the lysozyme concentration is greater than the 12 $\mu g$ per $\mu l$ value with corresponding decreases and increases as the L/S ratio decreases and increases. While the L/S ratio is at present the most accepted method of determining fetal lung maturity it requires both expensive laboratory equipment and trained personnel to determine it. The lysoplate method of this invention, however, as discussed above is both simple to use and is inexpensive.

EXAMPLE 2

170 Patients who were consecutively undergoing amniocentesis were chosen to demonstrate the effectiveness of the lysoplate method of this invention as compared to the L/S ratio method. For comparison purposes a third test known as the shake test, Clements et al., *N. Engl. J. Med.* 286: 1077, 1972 was also included. A sample sufficiently large to run all three tests was obtained from each patient. The patients were divided into groups based upon the results of the L/S ratio. The groups were broken down into those having an L/S ratio of less than 2 which included 75 individuals; those having an L/S ratio between 2.0 and 2.4 which included 44 individuals; those having an L/S ratio of 2.5 to 2.9 which included 36 individuals; and finally those having an L/S ratio of 3.0 to 4.1 which had 15 individuals.

When a 5 $\mu$l sample of amniotic fluid was used for the lysoplate test a minimal zone of lysis or minimal diffusion zone of 0.72±0.1 cm. which corresponds to a lysozyme concentration of 12 $\mu$g per $\mu$l was designated as the zone indicative of dividing the infants between those having mature lungs and those having immature lungs. Using this same sample size of amniotic fluid the ones with immature lungs had a lysis zone smaller than this figure and the ones with mature lungs had a lysis zone larger than this figure. Using this figure there were no false positives or negatives in the lysoplate test group as compared to the individuals having a less than 2.0 L/S ratio. In contrast the shake test had a false positive rate of 9.3 in this group. If one used the results of the shake test this would have resulted in the inappropriate management of these babies and possible severe sequelae associated with prematurity and respiratory distress syndrome.

In the L/S ratio group of 2.0 to 2.4 the lysoplate had no false positives and a false negative rate of 15% which compares very favorably with the false negative rate of 84% realized with the shake test. In the 2.5 to 2.9 L/S ratio group the lysoplate had no false positives or false negatives while the shake test had a false negative rate of 58.3%. Finally in the 3.0 to 4.1 L/S ratio group again the lysoplate had no false negatives or false positives in contrast to the shake test which had a false positive rate of 53%. Thus, when a 5 $\mu$l sample was used on the lysoplate and a zone of 0.72±0.1 cm. was chosen the lysoplate was a very reliable prognosticator of the condition of the fetal lungs which correlated well with the L/S ratio.

As the lysoplate test is very rapid and inexpensive it would be available to the clinician on a 24-hour basis indicating results with one-half hour and could be performed by personnel with only minimal training. The choice of sample size could be varied according to the wishes of the clinician, it only being necessary to run one standard lysozyme sample having the 12 $\mu$g per $\mu$l concentration to establish the appropriate zone of lysis which corresponds to the concentration of lysozyme which I have found to correspond to the L/S ratio of 2.

Another embodiment of the invention is the use of a polymeric material fashioned into some form convenient for assay purposes and coated with the assay medium. The lysozyme assay can be conducted with the coated polymeric material using observation procedures similar to those described hereinabove. The coated polymeric material can be in small test-strip form, similar to the test strips used to determine the sugar content or pH of urine. The small test strips can be brought into contact with a specimen to be tested in situ, thereby eliminating the necessity of withdrawing and transposing the specimen to a lysoplate. The coated polymeric test strips can be combined with other types of testing strips (for example, urine sugar and pH testing strips) into one multipurpose strip to afford convenience and time savings to the clinician and laboratory personnel.

I claim:

1. A method of determining the integrity of amniochorial membranes which comprises:
   collecting a sample of at least about one $\mu$l of vaginal fluid;
   placing said vaginal fluid sample in a concentrated area on the surface of a test plate wherein said test plate contains an agarose gel including within the gel a bactericidal agent and a suspension of killed Micrococcus lysodiekticus in a buffer containing an organic radical wherein the concentration of said buffer is from about 0.001 M to about 0.5 M and of an ionic strength which is of a strength sufficient such that said vaginal fluid sample dilutes the ionic strength of the point of contact of said vaginal fluid sample on the surface of said agarose gel to from about 0.05 to about 0.1;
   placing a standard quantity of a fluid containing a known concentration of a lysozyme on a second point on the surface of said agarose gel;
   incubating said test plate at about 37° C. from 20 minutes to 60 minutes;
   and comparing the size of the zone of lysis of said vaginal fluid sample with the size of the zone of lysis of said sample of lysozyme.

2. The method of claim 1 wherein:
   said incubation is performed for about 30 minutes, and said buffer is chosen from the group consisting of tris(hydroxymethyl) aminomethane maleate buffer, citrate buffer, citrate-phosphate buffer, imidazole hydrochloride sodium hydroxide buffer, and cacodylate buffer.

3. The method of claim 2 wherein:
   said sample of vaginal fluid is from about 5 to about 10 $\mu$l.

4. The method of claim 2 wherein:
   said sample of vaginal fluid is collected by contacting the walls of the vagina near the posterior fornix with a porous paper, said porous paper calibrated to absorb from about 5 to about 10 $\mu$l of vaginal fluidl 5. The method of claim 3 wherein:
   said paper is calibrated to absorb 5 $\mu$l of vaginal fluid.

6. The method of claim 2 wherein:
   after collecting said sample of vaginal fluid, said sample is deposited upon a small piece of porous paper on the surfce of said agarose gel.

7. The method of claim 1 wherein:
   said sample size is about 5 $\mu$l;
   said buffer concentration is about 0.05 M and is chosen from the group consisting of tris(hydroxymethyl) amino-methane maleate, citrate and citrate phosphate.

8. A composition for an assay plate determination of the lysozyme concentration of a biological sample which consists of:
   from about 0.5 percent to about 5 percent agarose;
   from about 0.03 to about 0.5 percent killed or attenuated Micrococcus lysodiekticus;
   from about 0.05 to about 0.1 percent bactercidal agent;
   in from about 0.001 M to about 0.5 M buffer containing an organic radical.

9. The composition of claim 8 wherein:
   the pH of said buffer is from about 6 to about 7 and the ionic strength of said buffer is from about 0.05 to about 0.01.

10. The composition of claim 9 wherein:

said buffer is chosen from the group consisting of tris(hydroxymethyl) aminomethane maleate buffer, citrate buffer, citrate-phospate buffer, imidazole hydrochloride sodium hydroxide buffer, and cacodylate buffer.

11. The composition of claim 9 wherein:
said buffer is chosen from the group consisting of tris(hydroxymethyl) aminomethane maleate buffer, citrate buffer, and citrate-phosphate buffer.

12. The composition of claim 10 wherein:
said bactericidal agent is sodium azide or thimerosal.

13. The composition of claim 10 wherein:
the pH of said buffer is from about 6.3 to 6.5.

14. The composition of claim 13 wherein:
said agarose concentration is about 0.05 percent, said *Micrococcus lysodiekticus* concentration is about 0.05 percent, said buffer concentration is about 0.05 M, and said ionic strength of said buffer is about 0.05.

15. A process for detecting and quantifying the content of the enzyme lysozyme in biological fluids which comprises:
placing a sample of said biological fluids on a test plate wherein said test plate contains from about 0.05 percent to about 5 percent agarose, from about 0.03 to about 0.5 percent killed *Micrococcus lysodiekticus*, from about 0.05 percent to about 0.1 percent bactericidal agent, in from about 0.01 M to about 0.5 M buffer containing an organic radical whose pH is from about 6 to about 7 and whose ionic strength is from about 0.05 to about 0.1;
placing a sample of a known concentration of purified lysozyme on an adjacent area on said test plate;
incubating said test plate at from about 25° C. to about 40° C. for about 20 minutes to about 60 minutes;
comparing the zone of lysis of said biological sample with the zone of lysis of said lysozyme sample.

16. The process of claim 15 wherein: said buffer is chosen from the group consisting of tris(hydroxymethyl) aminomethane maleate buffer, citrate buffer, citrate-phosphate buffer, imidazole hydrochloride sodium hydroxide buffer, and cacodylate buffer.

17. The process of claim 16 wherein:
said buffer has a pH of from about 6.3 to about 6.5, and said sample is incubated at about 37° C. for about 30 minutes.

18. The process of claim 17 wherein:
said agarose concentration is about 0.05 percent said *Micrococcus lysodiekticus* concentration is about 0.05 percent, said buffer concentration is about 0.05 M and said buffer ionic strength is about 0.05.

19. The process of claim 15 wherein:
said buffer is chosen from the group consisting of tris(hydroxymethyl)aminomethane maleate buffer, citrate buffer, and citrate-phosphate buffer.

20. A method of determining the maturity of fetal lumgs of an unborn fetus which comprises:
collecting a sample of amniotic fluid;
assaying said sample of amniotic fluid by using an assay procedure wherein the zone of lysis of a bactericidal cell is measured on a test plate, said plate containing a buffer having an organic radical in an amount sufficient to maintain the pH within a range suitable for cell lysis, to determine if the zone of lysis of the sample within one hour is greater than or less than the zone of lysis produced by a known sample of lysozyme having a concentration of 12 μg per ml.

21. The method of claim 20 wherein:
said sample is assayed by:
placing said amniotic fluid sample in a concentrated area on the surfce of a test plate wherein said test plate contains an agarose gel including within the gel a bactericidal agent and a suspension of killed *Micrococcus lysodiekticus* in said buffer wherein the concentration of said buffer is from about 0.001 M to about 0.5 M and of an ionic strength sufficient such that said amniotic fluid sample dilutes the ionic strength of the point of contact of said amniotic fluid sample on the surface of said agarose gel to from about 0.05 to about 0.1;
placing a standard quantity of a fluid containing 12 μg per m. of a lysozyme on a second point on the surface of said agarose gel;
incubating said test plate at about 37° C. for about 30 minutes;
and comparing the size of the zone of lysis of said amniotic fluid sample with the size of the zone of lysis of said sample of lysozyme.

22. The method of claim 20 wherein:
said bactericidal cell is *Micrococcus lysodiekticus* and the buffer is chosen from the group consisting of tris(hydroxymethyl) aminomethane maleate buffer, citrate buffer, citrate-phosphate buffer, imidazole hydrochloride sodium hydroxide buffer, and cacodylate buffer.

* * * * *

UNITED STATES PATENT AND TRADEMARK OFFICE
CERTIFICATE OF CORRECTION

PATENT NO. : 4,255,517

DATED : March 10, 1981

INVENTOR(S) : Larry C. Ford

It is certified that error appears in the above-identified patent and that said Letters Patent are hereby corrected as shown below:

On the cover sheet under Other Publications, line 2, delete "Analytial" and insert --Analytical--.

On the cover sheet under Other Publications, col. 2, line 1, delete "Bonauida" and insert --Bonavida--.

On the cover sheet under Other Publications, col. 2, line 3, delete "Bnetericidal" and insert --Bactericidal--.

On the cover sheet under Other Publications, col. 2, line 5, delete "Gynocol" and insert --Gynecol--.

On the cover sheet under Abstract, line 10, delete "by" and insert --By--.

In col. 3, line 54, delete "Petrie" and insert --Petri--.

In col. 5, line 39, delete "EXAMPLE" and insert --EXAMPLE 1--.

In col. 6, line 17, at the end of the line, delete "o" and insert --of--.

In col. 6, line 41, delete "35 weeks" and insert --37 weeks--.

In col. 7, line 23, delete "9.3" and insert --9.3%--.

UNITED STATES PATENT AND TRADEMARK OFFICE
CERTIFICATE OF CORRECTION

PATENT NO. : 4,255,517

DATED : March 10, 1981

INVENTOR(S) : Larry C. Ford

It is certified that error appears in the above-identified patent and that said Letters Patent are hereby corrected as shown below:

In col. 10, line 1, after the word percent, insert --,--.

In col. 10, line 10, delete "lumgs" and insert --lungs--.

In col. 10, line 36, delete "per m." and insert --per ml.--.

Signed and Sealed this

First Day of December 1981

[SEAL]

Attest:

GERALD J. MOSSINGHOFF

Attesting Officer     Commissioner of Patents and Trademarks